(12) United States Patent
Kloth et al.

(10) Patent No.: US 9,902,660 B2
(45) Date of Patent: Feb. 27, 2018

(54) PROCESSES FOR THE PREPARATION OF AN OLEFINIC PRODUCT

(71) Applicant: SHELL OIL COMPANY, Houston, TX (US)

(72) Inventors: Antonius Gijsbertus Johannes Kloth, Vaals (NL); Sivakumar Sadasivan Vijayakumari, Amsterdam (NL); Jeroen Van Westrenen, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/103,006

(22) PCT Filed: Dec. 13, 2013

(86) PCT No.: PCT/EP2013/076628
§ 371 (c)(1),
(2) Date: Jun. 9, 2016

(87) PCT Pub. No.: WO2015/086095
PCT Pub. Date: Jun. 18, 2015

(65) Prior Publication Data
US 2016/0355448 A1    Dec. 8, 2016

(51) Int. Cl.
*C07C 1/20* (2006.01)
*B01D 17/04* (2006.01)
*C10G 3/00* (2006.01)

(52) U.S. Cl.
CPC .............. *C07C 1/20* (2013.01); *B01D 17/045* (2013.01); *C10G 3/42* (2013.01); *C07C 2529/00* (2013.01); *C07C 2529/40* (2013.01); *C07C 2529/70* (2013.01); *Y02P 30/42* (2015.11)

(58) Field of Classification Search
CPC ........... C07C 1/20; C07C 11/02; C07C 11/04; C07C 11/06; C07C 2529/00; C07C 2529/40; C07C 2529/70; B01D 17/045; C10G 3/42
See application file for complete search history.

(56) References Cited

U.S. PATENT DOCUMENTS

| | | | |
|---|---|---|---|
| 4,567,029 A | 1/1986 | Wilson et al. | |
| 6,121,504 A | 9/2000 | Kuechler et al. | |
| 6,870,072 B2 * | 3/2005 | Lumgair .................. | C07C 1/20 585/639 |
| 2004/0152939 A1 * | 8/2004 | Pettigrew ................. | C07C 1/20 585/809 |
| 2005/0065390 A1 | 3/2005 | Van Egmond et al. | |
| 2007/0155999 A1 | 7/2007 | Pujado et al. | |
| 2007/0203380 A1 | 8/2007 | Vora et al. | |
| 2008/0161616 A1 | 7/2008 | Miller | |

FOREIGN PATENT DOCUMENTS

| | | |
|---|---|---|
| CN | 1852876 | 10/2006 |
| CN | 101868295 | 10/2010 |
| WO | 2006020083 | 2/2006 |
| WO | 2010104579 | 9/2010 |

OTHER PUBLICATIONS

International Search Report dated Aug. 22, 2014 of PCT/EP2013/076628 filed Dec. 13, 2013.

* cited by examiner

*Primary Examiner* — Sharon Pregler

(57) ABSTRACT

The invention provides a process for the preparation of an olefinic product, the process comprising the steps of: (a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products; (b) cooling the reaction effluent stream by means of an indirect heat exchange to provide a cooled reaction effluent stream at a temperature greater than the dew point temperature of reaction effluent stream; (c) passing the cooled reaction effluent stream into a quench tower and contacting the cooled reaction effluent stream with a first aqueous liquid in the presence of at least one set of quench tower internals, to produce a quench tower gaseous stream comprising the olefinic product and a quench tower liquid stream comprising condensed material; and (d) separating the quench tower liquid stream into a hydrocarbon quench tower liquid stream and an aqueous quench tower liquid stream in the presence of one or more coalescers.

9 Claims, 4 Drawing Sheets

PROCESSES FOR THE PREPARATION OF AN OLEFINIC PRODUCT

PRIORITY CLAIM

The present application is a National Stage (§ 371) application of PCT/EP2013/076628, filed 13 Dec. 2013, of which is hereby incorporated by reference in its entirety.

FIELD OF THE INVENTION

The present invention relates to a process for the preparation of an olefinic product, such as one or both of ethylene and propylene, from an oxygenate feedstock.

BACKGROUND OF THE INVENTION

Conventionally, ethylene and propylene are produced via steam cracking of paraffinic feedstocks comprising ethane or ethane/propane mixtures, known as gas cracking, or propane, butane, naphtha, NGL (natural gas liquids), condensates, kero, gas oil and hydrowax, known as naphtha cracking. An alternative route to ethylene and propylene is an oxygenate-to-olefin (OTO) process. Interest in OTO processes for producing ethylene and propylene is growing in view of the increasing availability of natural gas. Methane in the natural gas can be converted into, for instance, methanol or dimethylether (DME), both of which are suitable feedstocks for an OTO process.

In an OTO process, an oxygenate such as methanol or dimethylether is provided to a reaction zone of a reactor comprising a suitable conversion catalyst and is converted to ethylene and propylene. In addition to the desired ethylene and propylene, a substantial part of the oxygenate such as methanol is converted to higher hydrocarbons including C4+ olefins, paraffins and carbonaceous deposits on the catalyst. The catalyst is regenerated to remove a portion of the carbonaceous deposits by methods known in the art, for example heating the catalyst with an oxygen-containing gas such as air or oxygen.

The effluent from the reactor, comprising the olefins, any unreacted oxygenates such as methanol and dimethylether and other reaction products such as water, is separated from the bulk of the catalyst, usually by one or more cyclonic separation devices. The remaining effluent, may then be treated in a number of steps to provide separate component streams, including the desired olefin streams and by-product streams. Even after separation of the bulk of the catalyst, some solids, such as catalyst fines, will remain in the reaction effluent stream.

In order to increase the ethylene and propylene yield of the process, a separated stream containing C4+ olefins may be recycled to the reaction zone or alternatively further cracked in a dedicated olefin cracking zone to produce further ethylene and propylene.

Following reaction in the OTO reactor, the reaction effluent stream must be cooled before being treated to provide separate component streams. Conventionally, the reaction effluent stream is cooled to around 140 to 350° C. using one or more heat exchangers, often one or more transfer line exchangers (TLEs), before being contacted with a cooled aqueous stream in a quench tower. A quench tower comprises at least one set of internals such as packing and/or trays.

In usual operation, the gaseous stream to be quenched is fed into the quench tower below the internals and one or more cooled aqueous streams is fed into the quench tower above the internals. Thus, the gaseous stream travels upwards through the quench tower and is brought into contact with the one or more cooled aqueous streams travelling downwards through the tower (counter-currently to the gaseous stream). The cooled gaseous stream is removed from the top of the quench tower. An liquid stream containing condensed materials is removed at the bottom of the tower.

U.S. Pat. No. 6,870,072 describes such a quench tower process for recovering heat from the reaction effluent stream in an OTO process. In U.S. Pat. No. 6,870,072, the reaction effluent stream is quenched by contacting it with a quench medium, typically in a quench device, specifically a quench tower. The water cools the reactor effluent stream and removes solids. The water containing the solids is cooled and re-used as quench medium in the quench tower.

As well as aqueous material, liquid hydrocarbons and oxygenates will be present in the quench tower liquid stream. Solid material, such as catalyst fines may also be present. Separation of these different materials is carried out either in the bottom of the quench tower or in a separate settler. Solids are removed as a slurry. Liquid hydrocarbons are separated as a waste stream or for use as fuel. Aqueous material is separated and can be recycled, with cooling, to the quench tower or a different part of the process. A separated oxygenate containing liquid stream will usually be subjected to further separation in order to provide oxygenates for re-use as the oxygenate co-feed in the OTO reactor.

In known processes, separation of the aqueous material, solids and hydrocarbons is carried out by gravity separation using level control with a vertical weir. However, the presence of oxygenates in the quench tower liquid stream can cause difficult separation and foam formation, particularly in regions of turbulent flow.

It would be desirable to provide an improved process for the separation of the component materials in the quench tower liquid stream.

SUMMARY OF THE INVENTION

Accordingly, the present invention provides a process for the preparation of an olefinic product, the process comprising the steps of:
(a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products;
(b) cooling the reaction effluent stream by means of an indirect heat exchange to provide a cooled reaction effluent stream at a temperature greater than the dew point temperature of reaction effluent stream;
(c) passing the cooled reaction effluent stream into a quench tower and contacting the cooled reaction effluent stream with a first aqueous liquid in the presence of at least one set of quench tower internals, to produce a quench tower gaseous stream comprising the olefinic product and a quench tower liquid stream comprising condensed material; and
(d) separating the quench tower liquid stream into a hydrocarbon quench tower liquid stream and an aqueous quench tower liquid stream in the presence of one or more coalescers.

DETAILED DESCRIPTION OF THE INVENTION

Figure 1:
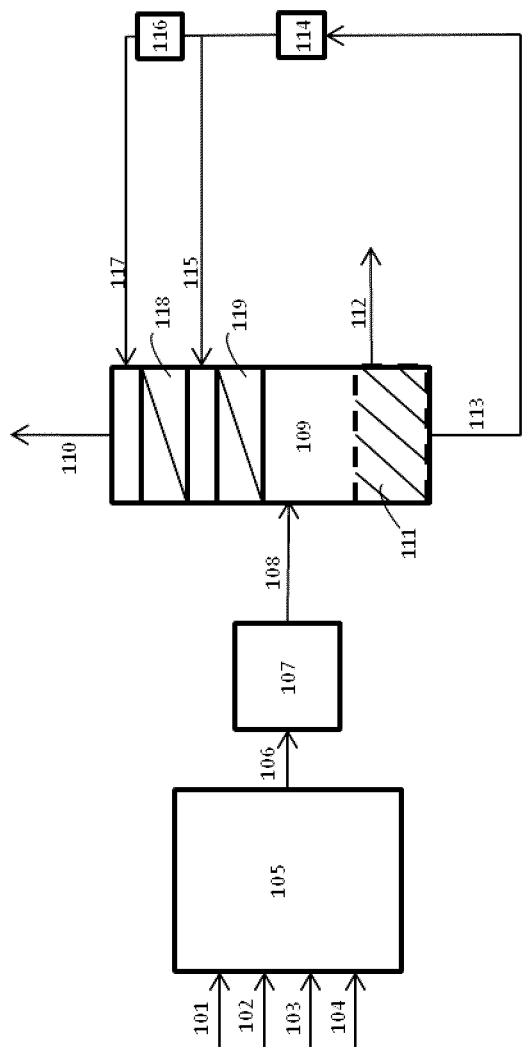
FIGS. 1 to 4 are schematic diagrams of exemplary, but non-limiting, embodiments of a process for the preparation of an olefinic product as described herein.

The present invention addresses the problems indicated by separating the liquid hydrocarbons from the aqueous quench tower liquid stream in the presence of a coalescer.

In step (b) the reaction effluent stream is cooled by means of an indirect heat exchange to recover the heat contained in the reactor effluent and to provide a cooled reaction effluent stream. Typically, the reaction effluent stream is indirectly contacted with a liquid stream, which is at a lower temperature, in a heat exchanger. The liquid stream is suitably a process stream, for instance a reactor feed, or a water stream. The heat exchanger may be of any type known in the art, for instance a transfer line exchanger (TLE) and/or a feed/effluent exchanger. Preferably, a shell and tube type heat exchanger is used.

In step (b) the reaction effluent stream is cooled to a temperature greater than the dew point of the reaction effluent stream. Preferably the reaction effluent stream is cooled to a temperature of no less than 110° C., preferably no less than 140° C., more preferably no less than 150° C., most preferably no less than 160° C. Preferably, the reaction effluent stream is cooled in step (b) to a temperature of at most 370° C., more preferably at most 320° C., more preferably at most 270° C., more preferably at most 250° C., even more preferably at most 240° C., even more preferably at most 220° C., even more preferably at most 200° C., even more preferably at most 190° C., most preferably at most 180° C.

In step (c), the cooled reaction effluent stream is fed into a quench tower at a point below any internals. The term internals, as used herein, preferably refers to packing and/or trays.

Gaseous material in the cooled reaction effluent stream will then pass upwards through the quench tower and contact a first aqueous liquid which is fed into the quench tower at one or more points above at least one set of internals. Preferably, the first aqueous liquid is fed into the quench tower at one or more points above each set of internals. After contacting the first aqueous liquid, the resultant quench tower gaseous stream is removed from the top of the quench tower.

All other materials present in the quench tower, including oxygenates, liquid hydrocarbons and aqueous materials will pass to the bottom of the quench tower. In step (d), these materials are separated into a hydrocarbon quench tower liquid stream and an aqueous quench tower liquid stream in the presence of one or more coalescers.

The separation may occur in the presence of a coalescer in the bottom of the quench tower. Alternatively, the separation may occur in the presence of a coalescer in a separate settler. In a further embodiment of the invention, the separation may occur in the presence of a coalescer in both the bottom of the quench tower and in the separate settler. In this embodiment of the invention, a first aqueous quench tower liquid stream is separated from the bottom of the quench tower and the remainder of the liquid material is passed to the separate settler for further separation and a second aqueous quench tower liquid stream will be removed from the separate settler. In this embodiment, the two separated aqueous quench tower liquid streams may be recycled to the same or different locations in the process. It may be advantageous to have two separate aqueous streams. Therefore, in this embodiment of the invention, it is preferable that the two separated aqueous quench tower liquid streams are recycled to different locations.

The coalescer is preferably a plate-type coalescer. Such coalescers are known in the art for the separation of liquid hydrocarbon/aqueous mixture. Preferably, the plate-type coalescer is selected from the group comprising corrugated plate interceptors (CPI), tilted plate interceptors (TPI), mesh packs, cross flow interceptors and combinations thereof.

Plate type coalescers depend on gravity separation to allow hydrocarbon droplets to rise to a plate surface where coalescence and capture can occur. Plate coalescers enhance coalescence of the oil droplets and, consequently, provide more efficient separation and require smaller cross-sectional areas thus providing space and weight gains over skim tanks.

CPIs comprise a series of corrugated parallel plates with the axes of the corrugations parallel to the direction of flow. A 'pack' of plates is inclined at an angle, preferably about 45°, forcing the liquid to flow downwards through the separator. The hydrocarbons rise upward counter to the water flow and are concentrated in the top of each corrugation and can be collected and separated.

In a preferred embodiment of the invention, the cooled reaction effluent stream is further cooled after step (b) and before step (c) by injection of a second aqueous liquid directly into the cooled reaction effluent stream. The second aqueous liquid is preferably water. It may suitably be fresh water, but preferably is a recycled stream from a later stage of the process for the preparation of an olefinic product.

Suitably, the second aqueous liquid is at a temperature of at least 10° C., preferably at least 20° C., most preferably at least 25° C. Suitably the second aqueous liquid is at a temp of at most 65° C., preferably at most 50° C., more preferably at most 40° C., most preferably at most 35° C.

The term 'direct injection' as used herein, indicates that the second aqueous liquid is provided straight into the cooled reaction effluent stream by a quench fitting suitable for dispersing the water into fine droplets, effectively forcing the liquid as fine droplets into the gas stream. The injection of the second aqueous liquid is co-current to the direction of flow of the cooled reaction effluent stream.

The second aqueous liquid is injected into the reaction effluent stream by means of a quench fitting. The quench fitting may be any means known in the art capable of rapidly introducing a large quantity of water directly into a gaseous stream, but suitably comprises a spray nozzle.

The second aqueous liquid is injected into the cooled reaction effluent stream such that the mass ratio of the second aqueous liquid to be injected to the total contents of the cooled reaction effluent stream is preferably at least 0.3:1, more preferably at least 1:1, most preferably at least 3:1. Preferably, the mass ratio of the second aqueous liquid to be injected to the total contents of the cooled reaction effluent stream is at most 20:1, more preferably at most 15:1, even more preferably at most 10:1, most preferably at most 8:1.

After cooling in this additional step, the cooled reaction effluent stream must be at a temperature at or below the dew point temperature of the reaction effluent stream. The dew point temperature of the reaction effluent stream will depend on the operating pressure of the system. Typically, the absolute operating pressure of the system at the point where the second aqueous liquid is injected into the reaction effluent stream by means of a quench fitting is at least 100 kPa, preferably at least 120 kPa, more preferably at least 140 kPa, typically at most 300 kPa, preferably at most 250 kPa, more preferably at most 200 kPa.

Preferably, the cooled reaction effluent stream is at a temperature of no more than 140 °C., more preferably no more than 130° C., most preferably no more than 125° C., most preferably no more than 115 °C. Preferably, the cooled reaction effluent stream is at a temperature of at least 50° C., more preferably at least 60° C., more preferably at least 70 °C., even more preferably at least 80° C., even more preferably at least 85° C., even more preferably at least 90° C., most preferably at least 95° C.

A liquid quench stream, comprising at least a portion of the second aqueous liquid as well as any condensed materials and solids present is then removed from the cooled reaction effluent stream, which has undergone further cooling. A portion of the second aqueous liquid may have evaporated in the process and form part of the cooled reaction effluent stream at this stage. The separation is suitably carried out in a separation vessel, such as a decanter or a knock out drum. The liquid quench stream is removed.

This embodiment of the invention has the added advantage that it prevents at least a portion of any solids present in the reaction effluent stream from entering the quench tower, reducing deposition of solids and blockages in the quench tower and coalescers.

The oxygenates containing liquid stream can be further separated to provide an oxygenate recovery stream for recycle as an oxygenate co-feed in the oxygenate reaction zone and a further aqueous recycle stream that can be cooled and used as the first aqueous liquid.

Reference herein to an oxygenate feedstock is to an oxygenate-comprising feedstock. In the oxygenate (or OTO) reaction zone, at least part of the feedstock is converted into a product containing one or more olefins, preferably including lower olefins, in particular ethylene and typically propylene.

The oxygenate used in the process is preferably an oxygenate which comprises at least one oxygen-bonded alkyl group. The alkyl group preferably is a C1-C5 alkyl group, more preferably C1-C4 alkyl group, i.e. comprises 1 to 5 or 1 to 4 carbon atoms respectively; more preferably the alkyl group comprises 1 or 2 carbon atoms and most preferably one carbon atom. Examples of oxygenates that can be used in the oxygenate feedstock include alcohols and ethers. Examples of preferred oxygenates include alcohols, such as methanol, ethanol, propanol; and dialkyl ethers, such as dimethyl ether, diethyl ether, methylethyl ether. Preferably, the oxygenate is methanol or dimethyl ether, or a mixture thereof.

Preferably, the oxygenate feedstock comprises at least 50 wt % of oxygenate, in particular methanol and/or dimethyl ether, based on total hydrocarbons, more preferably at least 70 wt %.

An oxygenate co-feed, comprising oxygenate recovered or produced in the process downstream of step (d) of the process of the present invention, such as an oxygenate recovered stream, may also be supplied, as discussed below. Such a stream may contain methanol, dimethyl ether and/or MTBE.

A diluent, such as water or steam, may also be provided to the oxygenate reaction zone. The molar ratio of oxygenate to diluent may be between 10:1 and 1:10, preferably between 4:1 and 1:2, in particular when the oxygenate is methanol and the diluent is water (typically steam).

Preferably, in addition to the oxygenate and diluent, an olefinic co-feed is provided along with and/or as part of the oxygenate feedstock. Reference herein to an olefinic co-feed is to an olefin-comprising co-feed.

The olefinic co-feed preferably comprises C4+ olefins i.e. C4 and higher olefins, more preferably C4 and C5 olefins.

In one preferred embodiment of the present invention, the olefinic co-feed comprises at least 30 wt %, preferably at least 50 wt %, more preferably at least 70 wt % of C4 hydrocarbon species. In this embodiment, the remainder of the olefinic co-feed comprises at least 70 wt %, more preferably at least 80 wt %, even more preferably at least 90 wt % C5 hydrocarbon species.

In a second preferred embodiment of the present invention, the olefinic co-feed comprises at least 50 wt %, preferably at least 70 wt % of C5 hydrocarbon species. In this embodiment, the remainder of the olefinic co-feed comprises at least 70 wt %, more preferably at least 80 wt %, even more preferably at least 90 wt % C4 hydrocarbon species.

Of the C4 hydrocarbon species present in the olefinic co-feed, preferably at least 35 wt %, more preferably at least 50 wt %, more preferably at least 75 wt % are olefins.

Of the C5 hydrocarbon species present in the olefinic co-feed, preferably at least 30 wt %, more preferably at least 45 wt % are non-cyclic olefins.

In order to maximize production of ethylene and propylene, it is desirable to maximize the recycle of C4 olefins in the effluent of the OTO process. This can be done by recycling at least part of the C4+ hydrocarbon fraction, preferably C4-C5 hydrocarbon fraction, more preferably C4 hydrocarbon fraction, in the OTO effluent. However, a certain part thereof, such as between 1 and 5 wt %, can be withdrawn as purge, since otherwise saturated hydrocarbons, in particular C4s (normal and iso butane) may build up in the process, which are substantially not converted under the OTO reaction conditions. Preferably, at least 70 wt % of the olefinic co-feed, during normal operation, is formed by a recycle stream of a C4+ hydrocarbon fraction from the OTO reaction effluent. Preferably, at least 90 wt % of olefinic co-feed, based on the whole olefinic co-feed, is formed by such recycle stream.

The preferred molar ratio of oxygenate in the oxygenate feedstock to olefin in the olefinic co-feed provided to the oxygenate reaction zone depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5, still more preferably in the range of 15:1 to 1:3, even still more preferably in the range of 12:1 to 1:3.

A variety of OTO processes are known for converting oxygenates, such as for instance methanol or dimethyl ether to an olefin-containing product, as already referred to above. One such process is described in WO 2006/020083. Processes integrating the production of oxygenates from synthesis gas and their conversion to light olefins are described in US 20070203380 and US 20070155999.

Catalysts suitable for converting the oxygenate feedstock comprise molecular sieve. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing tetrahedral units, more preferably, two or more $[SiO_4]$, $[AlO_4]$ and/or $[PO_4]$ tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico) aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably, the substituted metal atom (Me) is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a silica-to-alumina ratio, SAR, of at least 60, preferably at least 80. More preferred MFI-type zeolites have a silica-to-alumina ratio in the range of from 60 to 150, more preferably of from 80 to 100, Particular catalysts include catalysts comprising one or more zeolites having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50 wt %. of such zeolites based on total zeolites in the catalyst. In one embodiment, the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05 to 10 wt % based on the weight of the formulated catalyst. A particularly preferred catalyst comprises phosphorus and MEL or MFI-type zeolite having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

It is preferred that molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. It is well known in the art how to produce such molecular sieves in the hydrogen form.

The reaction conditions of the oxygenate conversion, include a reaction temperature of 350 to 1000° C., preferably from 350 to 750° C., more preferably 450 to 700° C., even more preferably 500 to 650° C.; and an absolute pressure from 0.1 kPa (1 mbar) to 5 MPa (50 bar), preferably from 100 kPa (1 bar) to 1.5 MPa (15 bar).

Preferably, the oxygenate feedstock is preheated to a temperature in the range of from 200 to 550° C., more preferably 250 to 500° C. prior to contacting with the molecular sieve-comprising catalyst.

The catalyst particles used in the process can have any shape known to the skilled person to be suitable for this purpose, and can be present in the form of spray dried catalyst particles, spheres, tablets, rings, extrudates, etc. Extruded catalysts can be applied in various shapes, such as, cylinders and trilobes. Spray-dried particles allowing use in a fluidized bed or riser reactor system are preferred. Spherical particles are normally obtained by spray drying. Preferably the average particle size is in the range of 1-200 μm, preferably 50-100 μm.

Although the C4+ hydrocarbon fraction in the reaction effluent may be recycled as an olefinic co-feed as discussed above, in an alternative embodiment, at least part of the olefins in the C4+ hydrocarbon fraction are converted to ethylene and/or propylene by contacting the C4+ hydrocarbon fraction in a separate unit with a molecular sieve-comprising catalyst, particularly a zeolite-comprising catalyst. This is particularly preferred where molecular sieve-comprising catalyst in the OTO process comprises a least one SAPO, AlPO, or MeAlPO type molecular sieve, preferably SAPO-34. These catalysts are less suitable for converting C4+ olefins.

Preferably, the C4+ hydrocarbon fraction is contacted with the zeolite-comprising catalyst at a reaction temperature of 350 to 1000° C., preferably from 375 to 750° C., more preferably 450 to 700° C., even more preferably 500 to 650° C.; and an absolute pressure from 0.1 kPa (1 mbar) to 5 MPa (50 bar), preferably from 100 kPa (1 bar) to 1.5 MPa (15 bar).

Optionally, the stream comprising C4+ olefins also contains a diluent. Examples of suitable diluents include, but are not limited to, liquid water or steam, nitrogen, argon, paraffins and methane. Under these conditions, at least part of the olefins in the C4+ hydrocarbon fraction are converted to further ethylene and/or propylene. The further ethylene and/or propylene may be combined with the further ethylene and/or propylene obtained directly from the oxygenate reaction zone. Such a separate process step directed at converting C4+ olefins to ethylene and propylene is also referred to as an olefin cracking process (OCP).

Catalysts comprising molecular sieve, particularly aluminosilicate-comprising catalysts, and more particularly zeolite-comprising catalysts, have the further advantage that in addition to the conversion of methanol or ethanol, these catalysts also induce the conversion of olefins to ethylene and/or propylene. Therefore, aluminosilicate-comprising catalysts, and in particular zeolite-comprising catalysts, are particularly suitable for use as the catalyst in an OCP. Particular preferred catalysts for the OCP reaction, i.e. converting part of the olefinic product, and preferably part of the C4+ hydrocarbon fraction of the olefinic product including C4+ olefins, are catalysts comprising at least one zeolite selected from MFI, MEL, TON and MTT type zeolites, more preferably at least one of ZSM-5, ZSM-11, ZSM-22 and ZSM-23 zeolites.

Both the OTO process and the OCP may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

The catalyst can deactivate in the course of the OCP and OTO process. The deactivation occurs primarily due to deposition of carbonaceous deposits, such as coke, on the catalyst by side reactions. The deactivated catalyst can be regenerated to remove a portion of the carbonaceous deposit by methods known in the art. It is not necessary, and indeed may be undesirable, to remove all the carbonaceous deposit from the catalyst as it is believed that a small amount of residual carbonaceous deposit such as coke may enhance the catalyst performance. Additionally, it is believed that complete removal of the carbonaceous deposit may also lead to degradation of the molecular sieve.

The same catalyst may be used for both the OTO process and OCP. In such a situation, the catalyst comprising molecular sieve, particularly comprising aluminosilicate molecular sieve and more particularly comprising zeolite, may be first used in the OCP reaction zone for the conversion of the C4+ olefins of the C4+ hydrocarbon fraction. The catalyst from the OCP may then be used, typically without regeneration, in the OTO process for conversion of an oxygenate feedstock and an olefinic co-feed. The deactivated catalyst from the OTO process may then be regenerated as described herein, and the regenerated catalyst then used again in the OCP.

This line-up may be beneficial because it provides good heat integration between the OCP, OTO and regeneration processes. The OCP is endothermic and at least a portion of the heat of reaction can be provided by passing catalyst from the regeneration zone to the OCP reaction zone, because the regeneration reaction which oxidizes the carbonaceous deposits from the loaded catalyst is exothermic.

Embodiments of the present invention will now be described by way of example only and with reference to the accompanying non-limiting figures.

It should be noted herein that, in the numbers on the Figures and referred to in the text, corresponding features on different Figures will have the same second and third digits in their indicative numbers, with the first digit referring to the Figure number. Thus, number 101 and 201 will refer to the same feature in FIGS. 1 and 2, respectively.

FIG. 1 exemplifies an embodiment of the present invention. An oxygenate feedstock 101 is fed into the oxygenate reaction zone 105. An oxygenate co-feed 102 may also be supplied by an oxygenate recovery stream. A diluent 103 may also be provided to the reaction zone. Preferably, an olefinic co-feed 104 is also provide to the reaction zone. The oxygenate co-feed, diluent and olefinic co-feed may be supplied to the reaction zone separately or one or more of these streams may be combined with the oxygenate feedstock or together before being fed to the reaction zone.

In the oxygenate (or OTO) reaction zone 105, reaction is carried out in the presence of a catalyst at a temperature in the range of from 350 to 1000° C. Following reaction, the gaseous product is separated from the bulk of the catalyst, e.g. by cyclonic separation devices, to produce a reaction effluent stream 106. The reaction effluent stream is cooled in one or more heat exchangers 107 situated in series, to provide a cooled reaction effluent stream 108 at a temperature greater than the dew point temperature of the reaction effluent stream and preferably in the range of from 150 to 250° C.

The cooled reaction effluent stream 108 is then fed into a quench tower 109 containing at least one set of internals and/or packing 118 and/or 119.

At least one first aqueous liquid stream 115, 117 is fed into the quench tower above the internals and/or packing. The cooled reaction effluent stream passes up through the internals and contacts the first aqueous liquid stream. A quench tower gaseous stream 110 comprising the olefinic product is removed from the top of the quench tower.

A quench tower liquid stream passes to the bottom of the quench tower and is separated into a hydrocarbon quench tower liquid stream 112 and an aqueous quench tower liquid stream 113 in the presence of a coalescer 111.

The aqueous quench tower liquid stream 113 is removed from the bottom of the quench tower 109 and may be cooled in a heat exchanger, e.g. air or water coolers 114 and 116 to provide the first aqueous liquid streams 115, 117.

Figure 2:
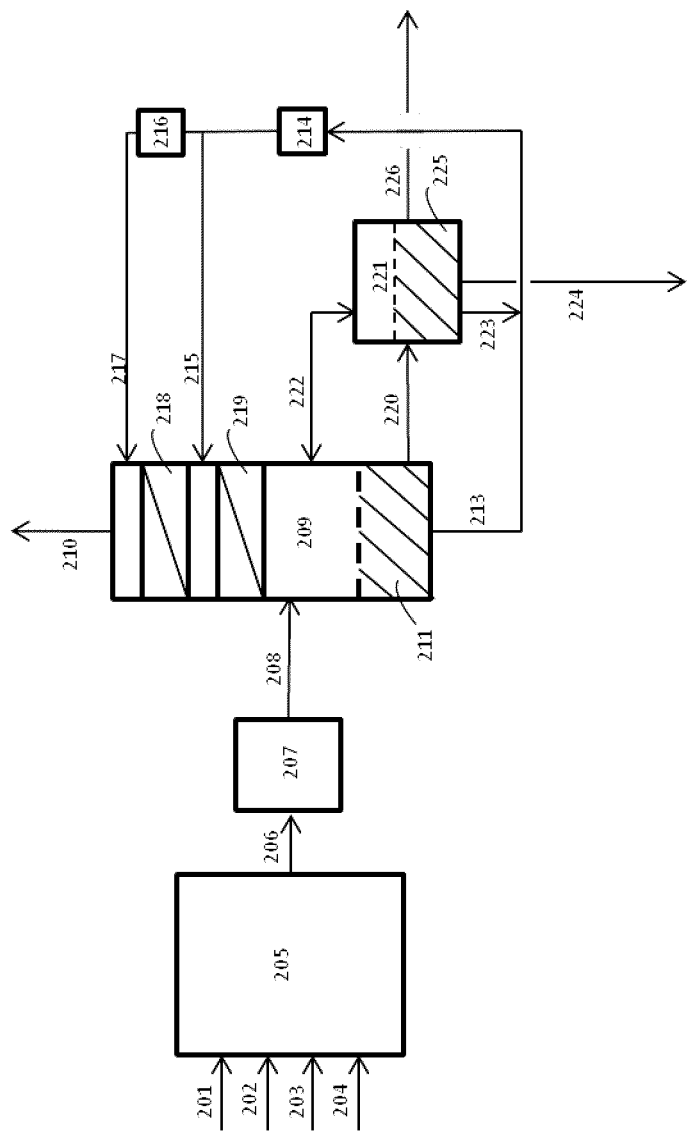

In the embodiment of the invention exemplified in FIG. 2, separation also occurs in a separate settler 221. A coalescer may be present in the separate settler 225, in the bottom of the quench tower 211 or in both.

A liquid stream 220 is removed from the bottom of the quench tower and passed to the separate settler 221. A pressure equalization line 222 may be present between settler and the quench tower. Aqueous material 223 is added to the aqueous stream for recycle. Liquid hydrocarbon stream 226 is separated and may be used as a waste stream or as fuel.

Solids 224 may also be removed from the separate settler, typically as a slurry.

Figure 3:
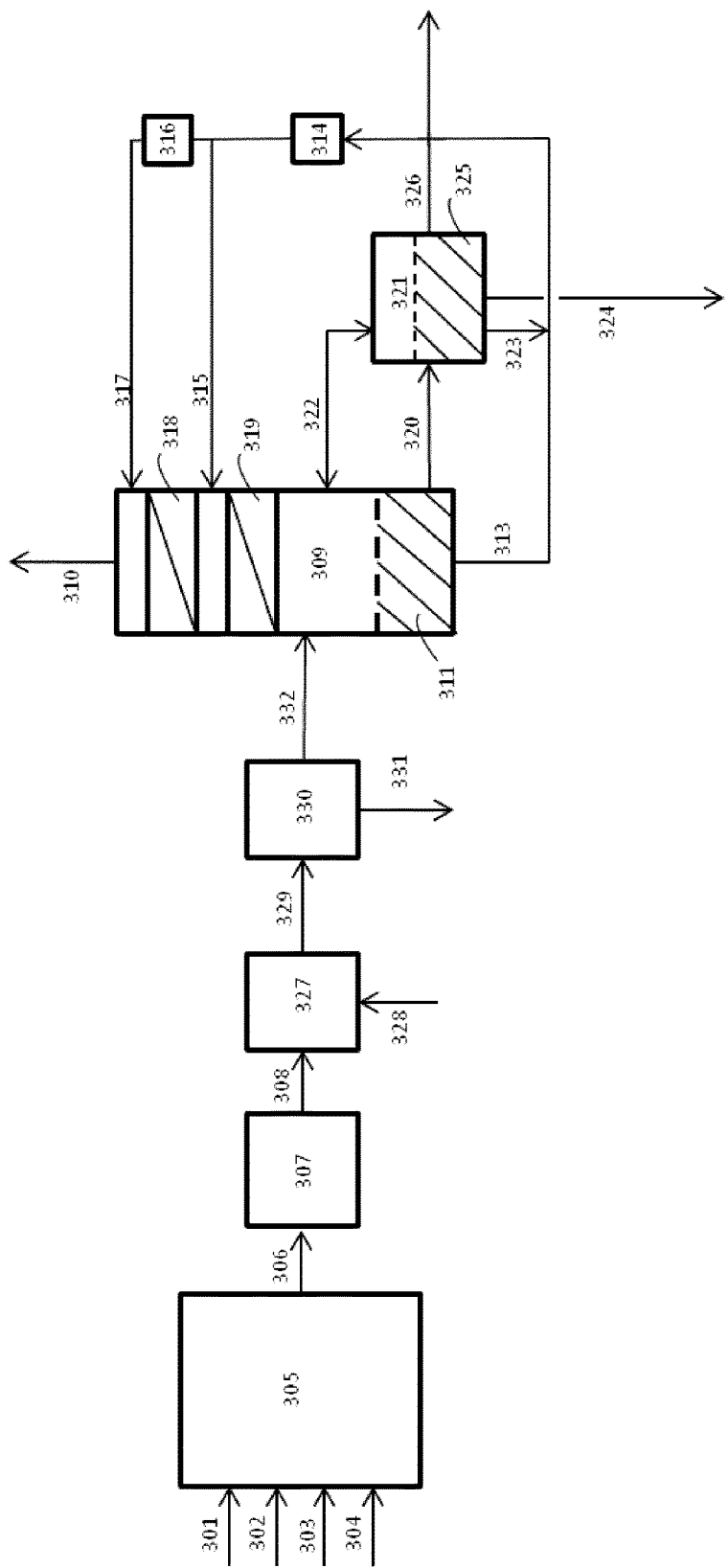

FIG. 3 shows an embodiment of the invention wherein, before the cooled reaction effluent stream is fed to the quench tower, it is contacted with a second aqueous liquid 328, which is directly injected into the cooled reaction effluent stream through a quench fitting (e.g. a spray nozzle) 327. The resultant stream 329 is then fed to a separation device 330 and a liquid quench stream 331 is separated. The thus treated cooled reaction effluent stream 332 is then passed to the quench tower 309.

Figure 4:
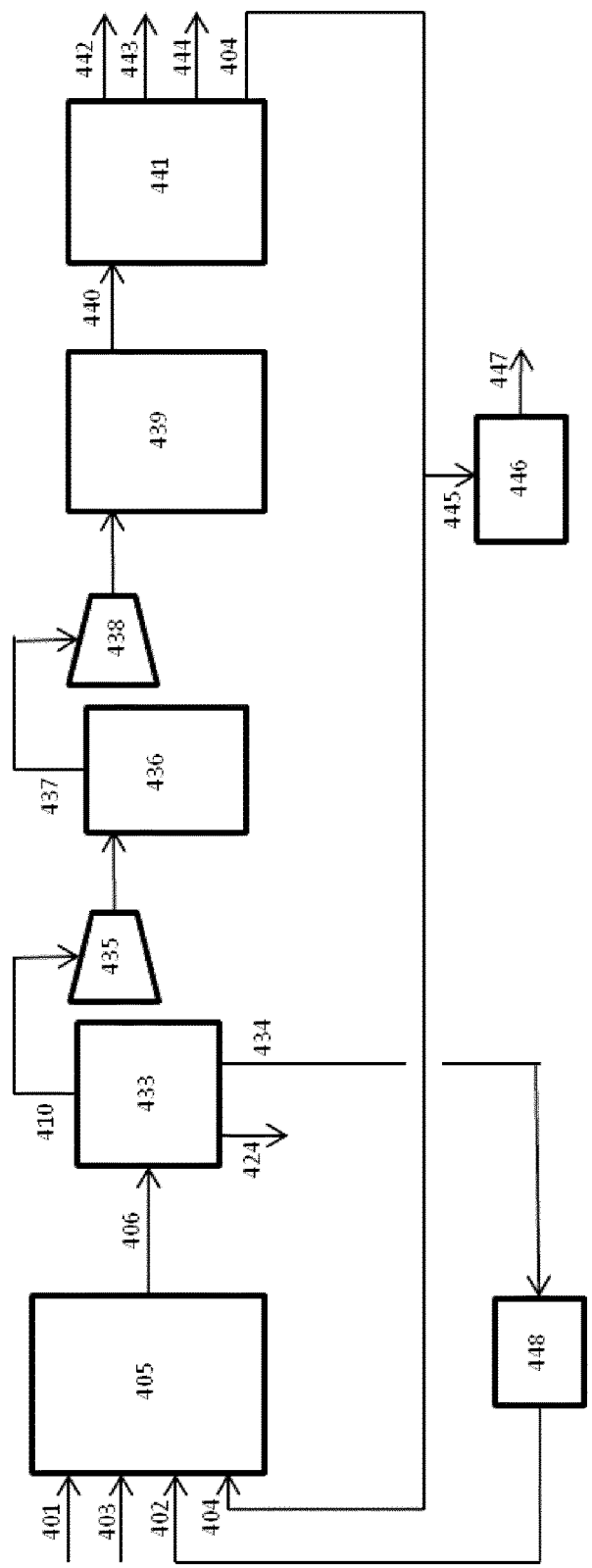

FIG. 4 shows one possible embodiment of the invention as it is incorporated into an overall process for the production of olefinic products such as ethylene and propylene. Oxygenate feedstock 401, an oxygenate co-feed 402, a diluent 403 and an olefinic co-feed 404 are provided to an oxygenate reaction zone 405. Reaction is carried out in the presence of a catalyst at elevated temperatures. The reaction product is separated from the catalyst to provide reaction effluent stream 406. The cooling and initial separation of steps (b), (c) and (d) of the present invention are carried out one or more times in series or in parallel to provide a quench tower gaseous stream 410. An oxygenate containing liquid stream 434 is also produced and can be subjected to separation and purification in the oxygenate separation zone 448 before being recycled as the oxygenate co-feed 402. A solid stream 424 is also produced.

The quench tower gas stream 410 is compressed in one or more gas compression stages 435 and is then passed to a carbonyl compound absorption zone 436 in which the stream is treated with a caustic solution to remove carbon dioxide and carbonyl compounds. The resultant stream 437 is further compressed in one or more compression stages 438 before being passed to water removal zone 439. After water removal, the remaining gas stream 440 enters an olefin separation zone 441 to be separated, preferably by one or more cryogenic distillation processes, to provide two or more olefinic component streams 442, 443, 444 and 404, including a stream comprising C4+ olefins which is recycled as olefinic co-feed 404.

In one alternative embodiment, all or part 445 of this stream 404 is subjected to an OCP 446 to provide a stream comprising ethylene and propylene 447. This stream 447 can then be fed back into the process as part of olefin rich gas stream 410.

That which is claimed is:

1. A process for the preparation of an olefinic product, the process comprising the steps of:
   a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products;
   b) cooling the reaction effluent stream by means of an indirect heat exchange to provide a cooled reaction effluent stream at a temperature greater than the dew point temperature of reaction effluent stream;
   c) passing the cooled reaction effluent stream into a quench tower and contacting the cooled reaction effluent stream with a first aqueous liquid in the presence of at least one set of quench tower internals, to produce a quench tower gaseous stream comprising the olefinic product and a quench tower liquid stream comprising condensed material; and
   d) separating the quench tower liquid stream into a hydrocarbon quench tower liquid stream and an aqueous quench tower liquid stream in the presence of one or more coalescers.

2. A process as claimed in claim 1, wherein at least a portion of the quench tower liquid stream is passed from the bottom of the quench tower to a separate settler.

3. A process according to claim 1, wherein a coalescer is present in the bottom of the quench tower.

4. A process according to claim 2, wherein a coalescer is present in the separate settler.

5. A process according to claim 1, wherein the coalescer is a plate-based coalescer.

6. A process according to claim 5, wherein the coalescer is selected from the group comprising corrugated plate interceptor, tilted plate interceptor, mesh pack, cross-flow interceptor and combinations thereof.

7. A process according to claim 1, wherein the cooled reaction effluent stream is further cooled after step (b) and before step (c) by injection of a second aqueous liquid directly into the cooled reaction effluent stream.

8. A process according to claim 7, wherein the second aqueous liquid is injected into the reaction effluent stream by means of a quench fitting.

9. A process according to claim 7, wherein a liquid quench stream, comprising at least a portion of the second aqueous liquid as well as any condensed materials and solids present, is removed from the cooled reaction effluent stream after injection of the second aqueous liquid and before step (c).

* * * * *